United States Patent [19]

Ward et al.

[11] Patent Number: 4,857,553
[45] Date of Patent: Aug. 15, 1989

[54] METHOD OF TREATING NAUSEA AND VOMITING WITH CERTAIN SUBSTITUTED-PHENYLALKYLAMINO (AND AMINOACID) DERIVATIVES AND OTHER SEROTONIN DEPLETING AGENTS

[75] Inventors: John W. Ward, Richmond, Va.; William L. Smith, Sunnyvale, Calif.

[73] Assignee: A. H. Robins Company, Incorporated, Richmond, Va.

[21] Appl. No.: 230,487

[22] Filed: Aug. 10, 1988

Related U.S. Application Data

[63] Continuation-in-part of Ser. No. 82,170, Aug. 6, 1987, abandoned.

[51] Int. Cl.$^4$ .................... A61K 31/19; A61K 31/135
[52] U.S. Cl. ....................................... 514/557; 514/646
[58] Field of Search ................................ 514/646, 557

*Primary Examiner*—Stanley J. Friedman

[57] ABSTRACT

A method for the treatment of emesis in a mammal, which method comprises administering to said mammal an emesis inhibiting amount of a compound which depletes serotonin in the brain of mammals; among which are compounds having the formula:

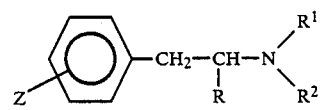

wherein, R is selected from hydrogen, loweralkyl, trifluoromethyl, carboxyl, or loweralkoxycarbonyl; $R^1$ and $R^2$ are hydrogen or loweralkyl; Z is trifluoromethyl or halogen; the optical isomers and pharmaceutically acceptable salts thereof; two of the preferred compounds of the invention are fenfluramine and norfenfluramine.

22 Claims, No Drawings

METHOD OF TREATING NAUSEA AND VOMITING WITH CERTAIN SUBSTITUTED-PHENYLALKYLAMINO (AND AMINOACID) DERIVATIVES AND OTHER SEROTONIN DEPLETING AGENTS

1. INTRODUCTION

The present invention relates to a novel method of controlling nausea and vomiting (or emesis) in mammals utilizing certain substituted-phenylalkylamino (and aminoacid) derivatives which do not exhibit certain side effects of the type attributable to dopamine blocking compounds which encompass fenfluramine, norfenfluramine and parachlorophenylalamine and other agents, e.g., reserpin which lower brain serotonin level.

The method of this invention comprises administering the subject compounds hereinbelow as therapeutic compositions which inhibit nausea and emesis induced by various stimulative effects. The compounds may be administered as a prophylactic prior to exposure to vomiting stimulus or after vomiting has started.

Needless to say it is highly desirable to use corrective agents such as the subject compounds which are free of serious extrapyramidal reactions associated with dopaminergic blockade observed with many prior art antiemetics inasmuch as vomiting subjects are frequently already in a traumatized condition.

2. BACKGROUND OF THE INVENTION

2.1 Kinetics of Nausea and Vomiting

Emesis is the final act of vomiting and may be described as the forceful expulsion of gastrointestinal contents through the mouth brought about by the descent of the diaphragm and powerful contractions of the abdominal muscles, triggered and coordinated by signals originating in the brain. Emesis is usually, but not always preceded by nausea and reteching. Nausea and vomiting may be caused by a number of stimulative factors including anesthetics, radiation, cancer chemotheraeutic agents, toxic agents, odors and psychological factors, reaction to various medicinals and motion sickness.

2.2 Prior Antiemetics

A number of antinausea and antiemetic agents are known. For example, phenothiazines as a class, including chlorpromazine and prochlorpromazine have had wide usage against emesis for a number of causal factors. In recent years, metoclopramide in relatively high dosage amounts has been the drug of choice in treating emesis caused by cancer chemotherapeutic agents. Still other agents which have had general antiemetic use are dimenhydrinate, meclozine and the cyclizine family which includes chlorcyclizine and bicyclizine. Many of the same drugs are effective in controlling motion sickness and in addition agents such as dexamphetamine (d-amphetamine), scopolamine and ephedrine are effective antiemetics against this phenomenon. However, Charles D. Wood in Drugs 17(6): 471–479(1979) indicates dexamphetamine and ephedrine are exceptions and not effective antiemetics against vomiting of toxic origins.

2.3 Prior Uses

Fenfluramine under the tradename Pondimin ® has been available as a prescription drug for a number of years as an appetite suppressant (anorexic) useful in the management of obesity in humans. Norfenfluramine is a metabolite of fenfluramine and has also been shown to have anorexic properties. Use of fenfluramine to bring about improvement in glucose tolerance in diabetic and nondiabetic patients has also been reported in Drugs 10(4): 241–328(1975) at page 296. Parachlorophenylalanine has been used to control diarrhea as reviewed in Goodman and Gilman's "The Pharmacological Basis of Therapeutics" 5th Ed. (1975) p. 620 published by Macmillan Publishing Co., Inc., Toronto, Canada and London, England.

There does not appear to be any connection with prior uses of compounds of Formula I and the newly discovered efficacy in controlling nausea and vomiting, considering what is known about their pharmacological properties and what was previously known about control of nausea and vomiting. Control of appetite and obesity by fenfluramine and norfenfluramine is thought to be related to release of serotonin from the brain and compounds such as p-chlorophenylalanine are known to be blockers of serotonin synthesis. Because prior art anti-emetic drugs such as metoclopramide have been considered to be dopaminergic antagonists by artisans in the field of pharmacology, it was unexpected to find that these agents useful in the present invention, which affect brain serotonin are effective antiemetics.

2.4 Problems Solved

Drugs used to control nausea and vomiting in the past have, for the most part, caused extrapyramidal reaction (side effects) of three types: parkinsonian syndrome, akathisia and tardive dyskinesia related to the antidopaminergic effect of the drugs. Heretofore, Reglan ®, a brand of metoclopramide salt, has been the drug of choice for use in controlling nausea and vomiting associated with administration of cancer chemotherapeutic agents including cisplatin, and the side effects associated therewith in some instances such as those described above are well recognized in the art. On the other hand, the compounds of Formula I do not have side-effects attributable to dopamine blockage (antidopaminergic effects) referred to above.

Fenfluramine and norfenfluramine when administered orally are more effective than metoclopramide administered orally and intravenous administration can thereby be avoided. Required doses of fenfluramine and norfenfluramine are lower in general, then those of metoclopramide, and therefore the chances for adverse reactions are lessened, which in the case of fenfluramine and norfenfluramine are of a minor nature. They also exhibit longer duration of effectiveness than metoclopramide, regardless of the method of administration, and require less frequency of adminstration compared to most known antiemetics.

3. SUMMARY OF THE INVENTION

3.1 The Discovery

The method of this invention is based on the discovery that compounds which have a depleting effect on brain serotonin or cause a lowering of intracellular serotonin when administered to animals have utility as antinauseants and antivomiting agents.

The compounds which are effective in the method of the invention fall into three classes:

a. Compounds which release brain serotonin such as compounds of Formula I represented by fenfluramine and norfenfluramine, and other compounds such as reserpine and tetrabenazine.

b. Compounds which inhibit synthesis of brain serotonin such as the Formula I compounds p-chlorophenylalanine and p-chloroamphetamine, and other compounds such as 6-fluorotrytophan.

c. Compounds which interfere with re-uptake of brain serotonin, illustrative of this type are trazodone and fluoxetine.

The phenylalkylamino derivatives within classes (a) and (b) supra, the formulas of which are shown below, can be used in the method of this invention to control nausea and vomiting when administered to mammals in need thereof. Use of the compounds is of particular benefit when used in conjunction with cancer chemotherapeutic agents, many of which (especially cisplatin) are known to be violently emetogenic. The compounds are also expected to be effective as antiemetics against emesis caused by chemotherapeutic agents administered in combinations. Confirmation of the anti-emetic effects of the compounds resides in the observations that emesis caused by apomorphine, high doses of cisplatin, and dacarbazine has been effectively controlled in dogs when moderate dosages of the compounds have been administered.

Effective dosages of the compounds of Formula I projected for emesis in man are of the same order as currently prescribed for anorexic utility and of less frequency. Inasmuch as side-effects attributable to dopaminergic blockage are not seen in anorexic treatment it its reasonable to project they will not be present in emesis control.

3.2 Generic Chemical Formula

The substituted-phenylalkylamino derivatives useful in the method of this invention are selected from those having the formula:

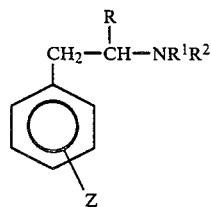

Formula I wherein
R is selected from hydrogen, loweralkyl, trifluoromethyl, carboxyl or loweralkoxycarbonyl;
$R^1$ and $R^2$ are hydrogen or loweralkyl;
Z is trifluoromethyl or halogen;
and optical isomers thereof,
and the pharmaceutically acceptable salts thereof.

3.3 The Pharmaceutical Method

The method of the invention comprises administering an effective amount of a compound which has a depleting effect on brain serotonin to control nausea and vomiting (emesis), usually in a pharmaceutically acceptable carrier, to mammalian subjects, including humans, which are in need of emesis control or can be expected to be in need of emesis control. Pharmaceutical compositions containing the compounds may be administered orally, parenterally, intramuscularly, intravenously, rectally, by inhalation, topically or subcutaneously, and in particular subjects so treated with a Formula I Compound are free of anti-dopaminergic side effects characteristically present with many known antiemetics.

Compounds of Formula I, supra, wherein R is hydrogen, loweralkyl or trifluoromethyl are preferred compounds and expected to be effective when administered either prior to or ofter a nausea and vomiting stimulative factor. The most preferred Formula I compounds of the invention have the formula:

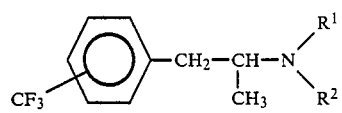

wherein, $R^1$ and $R^2$ are as defined under Formula I. They are preferred because of their propensity to low side effects.

Compounds of Formula I wherein R is carboxyl or loweralkoxycarbonyl are generally effective when administered prior to a nausea and vomiting stimulative factor.

4. DEFINITIONS

Certain terms used in the present discussion should at this point be mentioned to assure that the reader is of the same mind as the author as to their respective meanings. Thus the following definitions are provided to clarify the scope of the present invention, and to enable its formulation and use.

4.1 The term "halogen" refers to a member of the halogen family selected from chlorine, fluorine, bromine or iodine.

4.2 The term "loweralkyl" refers to straight and branched chain hydrocarbon radicals of one to five carbons inclusive and is exemplified by such groups as methyl, ethyl, propyl, isopropyl, butyl, sec butyl, tert butyl, anyl or isoamyl. The term "loweralkoxycarbonyl" has the formula —C(O)—O— loweralkyl.

4.3 The term "emesis" refers to the act of vomiting which more often than not includes nausea and retching prior to explusion through the mouth. The term "antiemetic" refers to an agent which prevents or stops emesis.

4.4 The terms "Fenfluramine," "N-ethyl-α-methyl-3-(trifluoromethyl)benzeneethanamine," "1'-(3'-trifluoromethylphenyl)-2-ethylaminopropane," and "1-(meta-trifluoromethylphenyl)-2-ethylaminopropane" refers to a chemical compound having the structure:

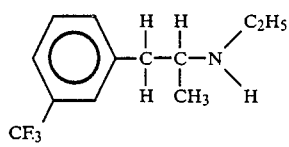

and as used in here may refer to optical isomers and pharmaceutically acceptable salts thereof. Pondimin ® is a trademark of A. H. Robins Company, Inc., for the monohydrochloride of a racemic mixture of d-fenfluramine and l-fenfluramine.

4.5 The terms "Norfenfluramine," and "1-(m-trifluoromethylphenyl)-2-aminopropane" refer to deethylated fenfluramine, and as used herein may refer to optical isomers and pharmaceutically acceptable salts thereof.

4.6 "Cancer chemotherapeutic agents" as used herein refers to a broad spectrum of antineoplastic agents which are known to cause emesis during attempts to cure cancer. Included among these agents are any of the platinum drugs, particularly cisplatin, and other agents as illustrated by dacarbazine, nitrogen mustard, cyclophosphamide, dactinomycin, 6-thioguanidine, carmustine, lomustine, methotrexate, 5-fluorouracil, vinblastine, aminoglutethimide, asparaginase, bleomycin, busulfan, cytarabine hydrochloride daunorubicin, doxorubicin, estramustine phosphate sodium, etoposide, floxuridine, fluorouracil, hydroxyurea, mercaptopurine, mitomycin, mitotane, plicamycin, procarbazine hydrochloride, streptozocin, tamoxifen citrate, and triethylenethiophosphoramide. As is recognized in the relevant art of treatment of neoplastic diseases, cancer chemotherapeutic agents are commonly used in combination.

4.7 By "akathisia" is meant the compelling need for the patient to be in constant movement rather than to any specific movement pattern.

4.8 By "tardive dyskinesia" is meant the neurological syndrome stereotyped by involuntary movements of jaws, tongue and limbs.

4.9 "Parkinsonian syndrome" refers to symptoms of generalized slowing of volitional movement or rigidity and tremor at rest.

4.10 The term "pharmaceutically acceptable salt" as used herein refers to and includes acid addition salts, hydrates, alcoholates, and salts of the compounds of Formula I which are physiologically compatible in mammals. The acid addition salts may be formed by either weak or strong acids. Representative of weak acids are fumaric, maleic, succinic, oxalic, citric, tartaric, cyclohexamic and the like. Representative of strong acids are hydrochloric, sulfuric, phosphoric and the like.

4.11 The term "optical isomers" as used herein refers to the levorotary and dextrorotary isomers of a Formula I compound, which exist when a chiral center is present in said Formula I compound.

4.12 The term "nausea and vomiting stimulative factor" as used herein includes anesthetics, radiation, cancer chemotherapeutic agents, toxic agents, odors, psycholoical factors, motion sickness, and the like.

5. DETAILED DESCRIPTION OF THE INVENTION

5.1 General Sources and Methods of Preparing Compounds

Certain of the Formula I compounds useful in the present invention are available commercially. Many others are known but unavailable commercially. In any event, compounds useful in the present invention may be prepared by synthetic methods and routes generally known to those skilled in the art. Several published methods are available for preparing the compounds but the scope of the invention is not limited thereto, however. It will be readily apparent to those skilled in the art, that variations in these methods of preparation are possible.

5.1.1 1-(Trifluoromethylphenyl)-1-loweralkyl-aminopropanes

U.S. Pat. No. 3,198,833 issued to Laszlo G. Beregi, et al., teaches methods of preparation for certain compounds of Formula I having the formula:

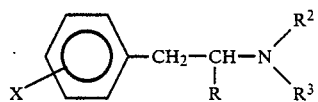

wherein
X is trifluoromethyl or fluoro;
R is trifluoromethyl or loweralkyl;
$R^1$ and $R^2$ are hydrogen or loweralkyl; and the pharmaceutically acceptable acid addition salts thereof. The methods of preparation of Formula I compounds taught in U.S. Pat. No. 3,198,833 are incorporated herein by reference.

5.1.2 Trifluoromethylphenylalkylamines

U.S. Pat. No. 3,078,307 issued to Paul N. Craig, et al., teaches methods of prepration for certain compounds of Formula I having the formula:

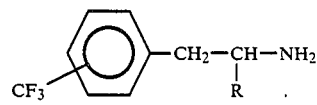

wherein R is hydrogen or methyl; and the pharmaceutically acceptable acid addition salts thereof. The methods of preparation of Formula I compounds taught in U.S. Pat. No. 3,078,307 are incorporated herein by reference.

5.1.3 α-Loweralkyl-2-Phenethylamines

Certain compounds of Formula I having the formula:

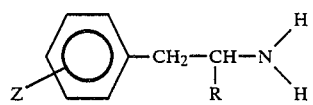

wherein Z is defined as under Formula I; and R is loweralkyl, may be prepared via an appropriate benzyl cyanide and grignard reagent as shown in the following equation:

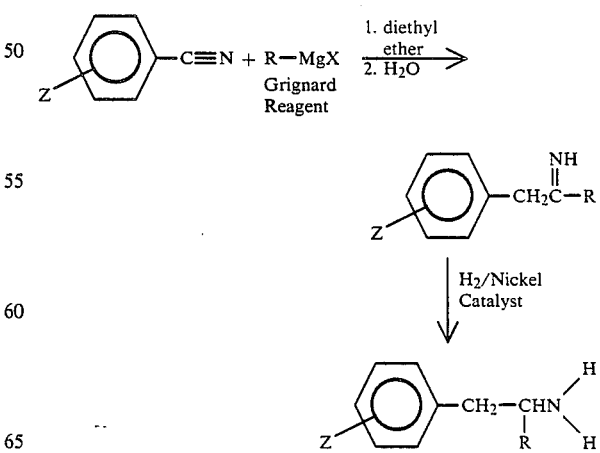

Many of the starting benzyl cyanides useful in this method are available commercially, e.g., see Section 5.2.5, infra, or may be prepared by methods generally known by those skilled in the art. Many of the desired grignard reagents are also available commercially or may be prepared by usual methods known in the art.

5.1.4 Phenylalanines

Methods of preparation for certain compounds of Formula I having the formula:

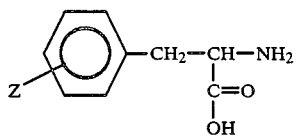

wherein z is halo; are taught in a paper by Leon Ghosez, et al., Tetrahedron Letters, Vol. 23, No. 41, pp. 4255–4258 (1982) and in a paper by Martin J. O'Donnell, et al., Synthesis, Vol. 4, April 1984, pp. 313–315. The methods of preparation of Formula I compounds taught in each of the above cited papers are incorporated herein by reference.

5.1.5 Phenylalanine Esters

Methods for the conversion of carboxylic acids into carboxylic acid esters are taught by R. T. Morrison and R. N. Boyd, Organic Chemistry, 3rd Ed., pp. 591, 602–603, Allyn and Bacon, Inc., Boston, Mass. (1973). The methods involved include conversion into esters via acid chlorides, and esterification by heating a desired carboxylic acid ester. Compounds of Formula I wherein R is a loweralkoxycarbonyl radical may be prepared by these methods from compounds of Formula I wherein R is carboxyl radical.

5.1.6 Separation of Isomers

Certain compounds of Formula I having the formula:

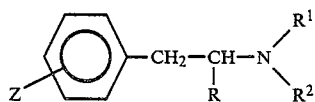

wherein, R is as defined under Formula I except hydrogen; and Z, $R^1$ and $R^2$ are as defined under Formula I; and the pharmaceutically acceptable salts thereof may exist in racemic mixtures containing 2 isomers. The racemic mixture may be denoted by DL, RS, dl, (±) or may simply be unqualified. Methods of separation and isolation of the different isomers are generally known to those skilled in the art. In any event, the following patents teach processes and are helpful in the separation of the optical isomers of the compounds of Formula I from a racemic mixture.

British Pat. No. 1,078,186 issued to Science Union Et Cie Societe Francaise De Recherche Medical, teaches separation of isomers from a racemic mixture of certain compounds of Formula I having the formula:

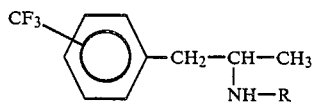

wherein R is loweralkyl. The method employs: (a) reacting the appropriate racemic amine compound with d-dibenzoyltartaric acid in the presence of a solvent to precipitate the d-dibenzoyltartaric acid salt of the l-isomer; (b) hydrolysing this salt under basic conditions to form the l-isomer; (c) treating the resolution liquor remaining after step (a)—after neutralizing and extracting by means of diethyl ether—with d-camphoric acid in the presence of a solvent to precipitate the d-camphoric acid salt of the d-isomer. Ethanol may be used as solvent in steps (a) and (c). The methods of separation for Formula I compounds taught in British Pat. No. 1,078,186 are incorporated herein by reference.

British Pat. No. 1,413,033 issued to V. W. Jacewicz, teaches a method for separation and resolution of norfenfluramine. This method employs:

(a) reacting a mixture of the (d)- and (l)-isomers of norfenfluramine with an optically pure dibenzoyltartaric acid in an organic solvent at an ambient or preferably elevated temperature;

(b) allowing or causing the resulting solution to cool to form a crystalline precipitate of the salt;

(c) recrystallizing the separated salt from an organic solvent which consists of methanol or contains a major proportion of methanol;

(d) treating the recrystallized salt under basic conditions to yield norfenfluramine in an optically active form.

in which process (l)-dizenzoyltartaric acid is used to prepare (l)-norfenfluramine and (d)-dibenzoyltartaric acid is used to prepare (d)-norfenfluramine. The methods of isolation of certain Formula I compounds taught in British Pat. No. 1,413,033 are incorporated herein by reference.

Normand L. Benoiton, et al. in U.S. Pat. No. 3,813,317 teaches a process for separation ring substituted phenylalanines by enzymatic resolution of racemic mixtures of substituted phenylalanines, via steps of esterification, enzymatic hydrolysis of the L-ester, recovery of liberated L-acid and optional hydrolysis and recycling of the D isomer. The methods of preparation taught by Benoiton in U.S. Pat. No. 3,813,317 for isomers of certain compounds of Formula I are incorporated herein by reference.

5.2 Specific Sources of Formula I Compounds

5.2.1 Formula I Compounds Available from Aldrich Chemical

The following Formula I compounds are available commercially from Aldrich Chemical Company, 940 West Saint Paul Avenue, Milwaukee, Wis. 53233 U.S.A.:

a. DL-4-bromophenylalanine,
b. DL-4-chlorophenylalanine,
c. L-4-chlorophenylalanine,
d. DL-4-chlorophenylalanine ethyl ester hydrochloride,
e. DL-4-chlorophenylalanine methyl ester hydrochloride,
f. DL-2-fluorophenylalanine,
g. DL-3-fluorophenylalanine,
h. DL-4-fluorophenylalanine,
i. D-4-fluorophenylalanine,
j. L-4-fluorophenylalanine,
k. D-4-iodophenylalanine,
l. DL-4-chloroamphetamine hydrochloride,
m. 4-bromophenethylamine,
n. 2-(2-chlorophenyl)ethylanine,
o. 2-(4-chlorophenyl)ethylamine, and p. 4-fluorophenethylamine hydrochloride.

5.2.2 Formula I Compounds Available from Pfaltz and Baur, Inc.

The Formula I compound, 2-(3-chlorophenyl)ethylamine is available commerically from Pfaltz & Baur, Inc., 172 E. Aurora St., Waterbury, CT 06708, U.S.A.

5.2.3 Formula I Compounds Preparable by Methods of U.S. Pat. No. 3,198,833

The following Formula I compounds were prepared by Beregi, et al:
a. 1-(4'-trifluoromethylphenyl)-2-aminopropane (See Ex. 1*, B.P. 49°–50° C.),
b. 1-(4'-trifluoromethylphenyl)-2-aminopropane hydrochloride (See Ex. 1*, M.P. 208°–210° C.)k,
c. 1-(4'-fluorophenyl)-3,3,3-trifluoro-2-aminopropane (See Ex. 2*, B.P. 90°–91° C.).
d. 1-(4'-fluorophenyl)-3,3,3-trifluoro-2-aminopropane hydrochloride (See. Ex. 2*, M.P. 210° C.),
e. 1-(4'-fluorophenyl)-2-dimethylaminopropane (See Ex. 3*, 93°–94° C.),
f. 1-(4'-fluorophenyl)-2-dimethylaminopropane hydrochloride (See Ex. 3*, M.P. 158°–160° C.),
g. 1-(3'-trifluoromethylphenyl)-2-dimethylaminopropane (See Ex. 3*, B.P. 99°–100° C.),
h. 1-(3'-trifluoromethylphenyl)-2-dimethylaminopropane hydrochloride (See Ex. 3*, M.P. 169°–170° C.),
i. 1-(4'-fluorophenyl)-2-ethylaminopropane (See Ex. 4*, B.P. 100°–102° C.),
j. 1-(4'-fluorophenyl)-2-ethylaminopropane hydrochloride (See. Ex. 4*, B.P. 154°–156° C.),
k. 1-(2'-fluorophenyl)-2-ethylaminopropane (See Ex. 4*, B.P. 98°–102° C.),
l. 1-(2'-fluorophenyl)-2-ethylaminopropane hydrochloride (See Ex. 4*, M.P. 149°–151° C.),
m. 1-(4'-fluorophenyl)-2-butylaminopropane (See Ex. 4*, B.P. 83°–88° C.),
n. 1-(4'-fluorophenyl)-2-butylaminopropane hydrochloride (See Ex. 4*, B.P. 193°–194° C.),
o. 1-(4'-trifluoromethylphenyl)-2-ethylaminopropane (See Ex. 5*, B.P. 109°–112° C.,
p. 1-(4'-trifluoromethylphenyl)-2-ethylaminopropane hydrochloride (See Ex. 5*, M.P. 202° C.),
q. 1-(3'-trifluoromethylphenyl)-2-ethylaminopropane (See Ex. 5, B.P. 108°–112° C.),

*Number refers to example number in U.S. Pat. No. 3,198,853.

5.2.4 Formula I Compounds Preparable by Methods of U.S. Pat. No. 3,078,307

The following Formula I compounds were prepared by Craig, et al:
a. 1-(p-trifluoromethylphenyl)-2-aminopropane hydrochloride (See Ex. 1*, M.P. 195°–197° C.),
b. p-trifluoromethylphenylethylamine (See Ex. 2*),
c. p-trifluoromethylphenylethylamine tartarate (See Ex. 2*),
d. 1-(m-trifluoromethylphenyl)-2-aminopropane hydrobromide (See Ex. 3*),
e. o-trifluoromethylphenylethylamine (See Ex. 5*), and
f. o-trifluoromethylphenylethylamine (See Ex. 5*).

*Number refers to example number in U.S. Pat. No. 3,078,307.

5.2.5 Preparation of Ring Substituted Amphetamines

When the following commerically available compounds:
a. 2-bromophenylacetonitrile (Aldrich Chemical),
b. 3-bromophenylacetonitrile (Aldrich Chemical),
c. 4-bromophenylacetonitrile (Aldrich Chemical),
d. 2-chlorobenzylcyanide (Aldrich Chemical),
e. 3-chlorobenzylcyanide (Aldrich Chemical), and
f. 4-chlorobenzylcyanide (Aldrich Chemical)
are reacted with methylmagnesium bromide, stepwise in (1) diethyl ether and (2) water, there are obtained:
a. 2-bromo-α-methylbenzeneethanimine,
b. 3-bromo-α-methylbenzeneethanimine,
c. 4-bromo-α-methylbenzeneethanimine,
d. 2-chloro-α-methylbenzeneethanimine,
e. 3-chloro-α-methylbenzeneethanimine, and
f. 4-chloro-α-methylbenzeneethanimine,
which are hydrogenated over nickel catalyst to give the following Formula I compounds:
a. DL-2-bromoamphetamine,
b. DL-3-bromoamphetamine,
c. DL-4-bromoamphetamine,
d. DL-2-chloroamphetamine,
e. DL-3-chloroamphetamine, and
f. DL-4-chloroamphetamine.

5.2.6 Preparation of Phenylalanine Ethyl Esters

When the following compounds from 5.2.1 above:
a. DL-4-bromophenylalanine,
b. L-4-chlorophenylalanine,
c. DL-2-fluorophenylalanine,
d. DL-3-fluorophenylalanine,
e. DL-4-fluorophenylalanine,
f. D-4-fluorophenylalanine,
g. L-4-fluorophenylalanine, and
h. D-4-iodophenylalanine
are esterified with excess ethol alcohol, the following ethyl esters are prepared:
a. DL-4-bromophenylalanine ethyl ester,
b. L-4-chlorophenylalanine ethyl ester,
c. DL-2-fluorophenylalanine ethyl ester,
d. DL-3-fluorophenylalanine ethyl ester,
e. DL-4-fluorophenylalanine ethyl ester,
f. D-4-fluorophenylalanine ethyl ester,
g. L-4-fluorophenylalanine ethyl ester, and
h. D-4-iodophenylalanine ethyl ester.

5.2.7 Preparation of DL-4-Chlorophenylalanine t-butyl ester

Part A

A heterogenous mixture of p-chlorobenzyl bromide (1.1 g, 0.005 mole) tetra-n-butylammonium bromide (0.9 g, 0.00565 mole), finely ground technical grade potassium carbonate (2.0 g, 0.015 mole) and acetonitrile (10 ml) is refluxed with stirring for 1 hr. The mixture is cooled, filtered, the solvent removed in vacuo, the residue dissolved in ether (15 ml), and then filtered. The ether is removed in vacuo at 20° C. and the residue dissolved in methanol (10 ml). Concentrated hydrochloric acid (0.0065 mole) is added to the stirred solution. After 1 hr, solid lithium hydroxide monohydrate (0.015 mole) is added and stirring continued overnight at 20° C. The solution is filtered, the pH is adjusted to 6 with concentrated hydrochloric acid. Two crops of crystals of p-chlorophenylalanine are collected; yield 0.69 g (60%).

*M. J. O'Donnell, et al., Synthesis, Vol. 4, No. 41, pp. 313–315.

Part B

The p-chlorophenylalanine prepared in Part A of this preparation is esterified with tertiary butyl alcohol to give the compound, DL-4-chlorophenylalanine tert-butyl ester.

5.2.8 Preparation of Phenylalanine t-butyl esters

Substituting the following commercially available compounds (Aldrich Chemical, Inc.):
a. α'-chloro-α,α,α-trifluoro-o-xylene,
b. α'-chloro-α,α,α-trifluoro-m-xylene,
c. α'-bromo-α,α,α-trifluoro-p-xylene,
d. 2-bromobenzylbromide,
e. 3-bromobenzylbromide,
f. 4-bromobenzylbromide,
g. 2-chlorobenzylbromide,
h. 3-chlorobenzylbromide,
i. 3-fluorobenzylbromide,
j. 3-fluorobenzylbromide,
k. 4-fluorobenzylbromide, and
l. 2-iodobenzylbromide
for p-chlorobenzylbromide in 5.2.7 there are obtained:
a. DL-2-trifluoromethylphenylalanine t-butyl ester,
b. DL-3-trifluoromethylphenylalanine t-butyl ester,
c. DL-4-trifluoromethylphenylalanine t-butyl ester,
d. DL-2-bromophenylalanine t-butyl ester,
e. DL-3-bromophenylalanine t-butyl ester,
f. DL-4-bromophenylalanine t-butyl ester,
g. DL-2-chlorophenylalanine t-butyl ester,
h. DL-3-chlorophenylalanine t-butyl ester
i. DL-2-fluorophenylalanine t-butyl ester,
j. DL-3-fluorophenylalanine t-butyl ester,
k. DL-4-fluorophenylalanine t-butyl ester, and
l. DL-2-iodophenylalanine t-butyl ester.

5.2.9 Preparation of Norfenfluramine Isomers

Part A

(d)-Norfenfluramine

Racemic norfenfluramine free base extracted from the hydrochloride salt (1.7 g) was added slowly to a solution of anhydrous dibenzoyl-1 tartaric acid (3 g) in dry boiling methanol (15 ml). Slow crystallization gave the crystalline dibenzoyltartrate (0.38 g).

Recrystallization from dry methanol (15 ml) gave a fine crystalline product (ca. 100 mg) from which resolved norfenfluramine was liberated with aqueous sodium hydroxide, extracted into ether, the ether layer dried and treated with dry hydrogen chloride gas to precipitate the hydrochloride salt. This was recrystallized from dry ethanol/ether to give pure (d)-norfenfluramine hydrochloride (25.0 mg), [1.5%], melting point 173°–173.5° C., $[\alpha]_D^{20}$ [3% in methanol] = +7.55°).

Part B

(l)-Norfenfluramine

Norfenfluramine free base (21.3 g) was added slowly to a boiling solution of dibenzoyl d-tartaric acid (42.6 g) in dry ethanol (350 ml). Slow cooling gave a crystalline precipitate of the salt (11.1 g). Recrystallization of 25.4 g norfenfluramine dibenzoyl-d-tartarate from dry methanol (800 ml), gave a crystalline product (8.10 g) which was dried, suspended in water, basified with aqueous sodium hydroxide, extracted into ether to give, on evaporation, crude (l)-norfenfluramine as an oil. Passing dry hydrogen chloride gas through an ether solution precipitated the hydrochloride salt which, on recrystallizing from dry ethanol/ether, gave pure (l)-norfenfluramine hydrochloride (4.2 g, [7.4%], melting point 172.5°–173.5° C., $[\alpha]_D^{20}$ [5% in methanol] = −7.61°).

5.2.10 Preparation of Fenfluramine Isomers

Part A

(l)-Fenfluramine

To a solution of 160 parts of d-dibenzoyltartaric acid and 1600 parts of anhydrous ethanol were added, over a period of 15 minutes, 80 parts of dl 1-(meta-trifuoromethylphenyl)-2-ethylaminopropane. After 15 additional minutes, 90.5 parts of crystalline solid were isolated.

When this product was recrystallized from 1300 parts of anhydrous ethanol, there are obtained 70 parts of the dibenzoyl d-tartarate acid salt of (l)-1-(meta-trifluoromethylphenyl)-2-ethylaminopropane.

The salt obtained as described above was treated with 500 parts of 4 normal aqueous sodium hydroxide solution. The mixture was extracted with two 200-part portions of diethyl ether and the ether extract was re-extracted with 100 parts of 4 normal hydrochloric acid. After treatment with 120 parts of 4 normal aqueous sodium hydroxide solution, the free amine amounting to 25 parts distills at 105°–107° C. (17.5 mm). Rotation $(\alpha)_D^{25}$: −9.6° (8% in ethyl alcohol).

The (l)-1-(meta-trifluoromethylphenyl)-2-ethylaminopropane hydrochloride melted at 160°–161° C. (ethyl acetate).

Part B

(d)-Fenfluramine

The mixture from Part A was extracted with two 250-part portions of diethyl ether. After acidification with 100 parts of 4 normal hydrochloric acid and separation, the aqueous layer was treated with 120 parts of 4 normal aqueous sodium hydroxide solution and finally extracted with two 250-part portions of diethyl ether. The extract was dried over magnesium sulfate and then freed of diethyl ether by distillation. Rotation of the residue (30 parts) after vacuum distillation gave an $(\alpha)_D^{23}$ of +7.1°; [8% in ethyl alcohol]. Seventeen parts of the crude amine obtained were added to 17 parts of (d)-camphoric acid dissolved in 160 parts of anhydrous ethanol. After 3 hr, 20 parts of precipitate separated which was recrystallized from 120 parts of anhydrous ethanol. This (d)-camphoric acid salt of (d)-1-(metatrifluoromethylphenyl)-2-ethylaminopropane, after treatments as described above for the lavorotary isomer, gave 9 parts of the desired amine $(\alpha)_D 25$: +9.5° (8% in ethanol).

The (d)-1-(meta-trifluoromethylphenyl)-2-ethylaminopropane hydrochloride melted at 160°–161° C. (ethyl acetate).

Table of Formula I Compounds

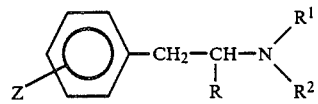

| Compound No. | Z | R | R² | Isomers | Salt |
|---|---|---|---|---|---|
| 5.2.1-a. | 4-Br | —C(O)—OH | —NH₂ | DL | — |
| 5.2.1-b. | 4-Cl | —C(O)—OH | —NH₂ | DL | — |
| 5.2.1-c. | 4-Cl | —C(O)—OH | —NH₂ | L | — |
| 5.2.1-d. | 4-Cl | —C(O)—O—C₂H₅ | —NH₂ | DL | HCl |
| 5.2.1-e. | 4-Cl | —C(O)—O—CH₃ | —NH₂ | DL | HCl |
| 5.2.1-f. | 2-F | —C(O)—OH | —NH₂ | DL | — |
| 5.2.1-g. | 3-F | —C(O)—OH | —NH₂ | DL | — |
| 5.2.1-h. | 4-F | —C(O)—OH | —NH₂ | DL | — |
| 5.2.1-i. | 4-F | —C(O)—OH | —NH₂ | D | — |
| 5.2.1-j. | 4-F | —C(O)—OH | —NH₂ | L | — |
| 5.2.1-k. | 4-I | —C(O)—OH | —NH₂ | D | — |
| 5.2.1-l. | 4-Cl | —CH3 | —NH₂ | DL | HCl |
| 5.2.1-m. | 4-Br | H | —NH₂ | — | — |
| 5.2.1-n. | 2-Cl | H | —NH₂ | — | — |
| 5.2.1-o. | 4-Cl | H | —NH₂ | — | — |
| 5.2.1-p. | 4-F | H | —NH₂ | — | HCl |
| 5.2.2 | 3-Cl | H | —NH₂ | — | — |
| 5.2.3-a. | 4-CF₃ | —CH₃ | —NH₂ | DL | — |
| 5.2.3-b. | 4-CF₃ | —CH₃ | —NH₂ | DL | HCl |
| 5.2.3-c. | 4-F | —CF₃ | —NH₂ | DL | — |
| 5.2.3-d. | 4-F | —CF₃ | —NH₂ | DL | HCl |
| 5.2.3-e. | 4-F | —CH₃ | —N(CH₃)₂ | DL | — |
| 5.2.3-f. | 4-F | —CH₃ | —N(CH₃)₂ | DL | HCl |
| 5.2.3-g. | 3-CF₃ | —CH₃ | —N(CH₃)₂ | DL | — |
| 5.2.3-h. | 3-CF₃ | —CH₃ | —N(CH₃)₂ | DL | HCl |
| 5.2.3-i. | 4-F | —CH₃ | —NH(C₂H₅) | DL | — |
| 5.2.3-j. | 4-F | —CH₃ | —NH(C₂H₅) | DL | HCl |
| 5.2.3-k. | 2-F | —CH₃ | —NH(C₂H₅) | DL | — |
| 5.2.3-l. | 2-F | —CH₃ | —NH(C₂H₅) | DL | HCl |
| 5.2.3-m. | 4-F | —CH₃ | —NH(C₄H₉) | DL | — |
| 5.2.3-n. | 4-F | —CH₃ | —NH(C₄H₉) | DL | HCl |
| 5.2.3-o. | 4-CF₃ | —CH₃ | —NH(C₂H₅) | DL | — |
| 5.2.3-p. | 4-CF₃ | —CH₃ | —NH(C₂H₅) | DL | HCl |
| 5.2.3-q. | 3-CF₃ | —CH₃ | —NH(C₂H₅) | DL | — |
| 5.2.3-r. | 3-CF₃ | —CH₃ | —NH(C₂H₅) | DL | HCl |
| 5.2.4-a. | 4-CF₃ | —CH₃ | —NH₂ | DL | HCl |
| 5.2.4-b. | 4-CF₃ | H | —NH₂ | — | — |
| 5.2.4-c. | 4-CF₃ | H | —NH₂ | — | tartarate |
| 5.2.4-d. | 3-CF₃ | —CH₃ | —NH₂ | DL | HBr |
| 5.2.4-e. | 2-CF₃ | H | —NH₂ | — | — |
| 5.2.4-f. | 2-CF₃ | H | —NH₂ | — | acetate |
| 5.2.5-a. | 2-Br | —CH₃ | —NH₂ | DL | — |
| 5.2.5-b. | 3-Br | —CH₃ | —NH₂ | DL | — |
| 5.2.5-c. | 4-Br | —CH₃ | —NH₂ | DL | — |
| 5.2.5-d. | 2-Cl | —CH₃ | —NH₂ | DL | — |
| 5.2.5-e. | 3-Cl | —CH₃ | —NH₂ | DL | — |
| 5.2.5-f. | 4-Cl | —CH₃ | —NH₂ | DL | — |
| 5.2.6-a. | 4-Br | —C(O)—O—C₂H₅ | —NH₂ | DL | — |
| 5.2.6-b. | 4-Cl | —C(O)—O—C₂H₅ | —NH₂ | L | — |
| 5.2.6-c. | 2-F | —C(O)—O—C₂H₅ | —NH₂ | DL | — |
| 5.2.6-d. | 3-F | —C(O)—O—C₂H₅ | —NH₂ | DL | — |
| 5.2.6-e. | 4-F | —C(O)—O—C₂H₅ | —NH₂ | DL | — |
| 5.2.6-f. | 4-F | —C(O)—O—C₂H₅ | —NH₂ | D | — |
| 5.2.6-g. | 4-F | —C(O)—O—C₂H₅ | —NH₂ | L | — |
| 5.2.6-h. | 4-I | —C(O)—O—C₂H₅ | —NH₂ | D | — |
| 5.2.7 | 4-Cl | —C(O)—O—C(CH₃)₃ | —NH₂ | DL | — |
| 5.2.8-a. | 2-CF₃ | —C(O)—O—C(CH₃)₃ | —NH₂ | DL | — |
| 5.2.8-b. | 3-CF₃ | —C(O)—O—C(CH₃)₃ | —NH₂ | DL | — |
| 5.2.8-c. | 4-CF₃ | —C(O)—O—C(CH₃)₃ | —NH₂ | DL | — |
| 5.2.8-d. | 2-Br | —C(O)—O—C(CH₃)₃ | —NH₂ | DL | — |
| 5.2.8-e. | 3-Br | —C(O)—O—C(CH₃)₃ | NH₂ | DL | — |
| 5.2.8-f. | 4-Br | —C(O)—O—C(CH₃)₃ | NH₂ | DL | — |
| 5.2.8-g. | 2-Cl | —C(O)—O—C(CH₃)₃ | NH₂ | DL | — |
| 5.2.8-h. | 3-Cl | —C(O)—O—C(CH₃)₃ | NH₂ | DL | — |
| 5.2.8-i. | 2-F | —C(O)—O—C(CH₃)₃ | NH₂ | DL | — |
| 5.2.8-j. | 3-F | —C(O)—O—C(CH₃)₃ | NH₂ | DL | — |
| 5.2.8-k. | 4-F | —C(O)—O—C(CH₃)₃ | —NH₂ | DL | — |
| 5.2.8-l. | 2-I | —C(O)—O—C(CH₃)₃ | —NH₂ | DL | — |
| 5.2.9-a. | 3-CF₃ | —CH₃ | —NH₂ | D | HCl |

-continued
Table of Formula I Compounds

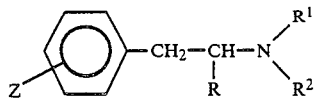

| Compound No. | Z | R | —NR¹R² | Isomers | Salt |
|---|---|---|---|---|---|
| 5.2.9-b. | 3-CF$_3$ | —CH$_3$ | —NH$_2$ | L | HCl |
| 5.2.10-a. | 3-CF$_3$ | —CH$_3$ | —NHC$_2$H$_5$ | L | HCl |
| 5.2.10-b. | 3-CF$_3$ | —CH$_3$ | —NHC$_2$H$_5$ | D | HCl |

6. TEST PROCEDURES AND RESULTS

Two test procedures A and B were used to show the antiemetic effectiveness and utility of compounds in this invention.

6.1 Test Procedure A (Emesis Induced by Cancer Chemotherapeutic Agents, Protoveratrine A or Copper Sulfate)

The test procedure is a modification of that used by Gylys, J. A., et al. Res. Chem. Pathol. Pharmacol. 23, No. 1, 61–68 (1979). Tests were performed on groups of at least 4 adult mongrel non-fasted dogs of both sexes, with an equal number of dogs serving as test animals and controls. The Formula I compound or other test compound [or in the case of controls (distilled water)] were administered either 30 minutes prior, or 60 minutes after intravenous administration of 3.0 mg/kg cisplatin or a known chemotherapeutic amount of other emesis inducing antineoplastic drug, e.g., 30 mg/kg dacarbazine, or 100 mg/kg of Protoveratrine A orally or 20 mg/kg of copper sulfate orally. Dogs were observed for 5 hr after the administration of cisplatin or other known emesis inducing antineoplastic drug, e.g., dacarbazine, or other emesis producing compound, e.g., Protoveratrine A or copper sulfate, and the number of emetic episodes recorded for dogs receiving Formula I compound or other test compound or distilled water (controls). Results were expressed as percent inhibition of emetic episodes and calculated using the equation:

$$1 - \frac{\text{No. Emetic Episodes - Test Dogs}}{\text{No. Emetic Episodes - Control Dogs}} \times 100 = \% \text{ Inhibition}$$

A further modification in this procedure is required when compounds of Formula I wherein R is carboxyl or loweralkoxycarbonyl are administered. This further modification is similar to a procedure taught by Koe, et al., used to deplete brain serotonin in dogs.* The procedure modifications used herein consist of administering Formula I compounds orally (100 mg/kg) in a hard gelatin capsule shell, once a day for 9 consecutive days (control animals receive empty capsule shells). On day 10 the desired emesis inducing antineoplastic drug or other emesis producing compound is administered.
*J. Pharmacol. Exp. Ther., 154(4), pp. 449–516 (1966).

6.2 Test Procedure B (Apomorphine Induced Emesis)

The test procedure is a modification of that used by Chen and Ensor, J. Pharmacol. Exp. Ther. 98, 245–250 (1950). Eight adult mongrel dogs of both sexes (fasted 18 hr prior to the start of study) were given apomorphine 100 µg/kg subcutaneously to establish a control response. On the test day, Formula I compounds to be tested were administered intravenously 30 minutes prior to the subcutaneous administration of 100 µg/kg apomorphine. Dogs were observed for 1 hr following administration of apomorphine and the number of emetic episodes recorded for dogs receiving Formula I test compounds. Results were expressed as percent inhibition of emetic episodes, and calculated using the equation:

$$1 - \frac{\text{No. Emetic Episodes - Test Dogs}}{\text{No. Emetic Episodes - Control Dogs}} \times 100 = \% \text{ Inhibition}$$

A further modification in this procedure is required when compounds of Formula I wherein R is carboxyl or loweralkoxycarbonyl are administered. This further modification is similar to a procedure taught by Koe, et al., used to deplete brain serotonin in dogs.* The procedure modifications used herein consist of administering Formula I compounds orally (100 mg/kg) in a hard gelatin capsule shell, once a day for 9 consecutive days (control animals receive empty capsule shells). On day 10, 100 µg/kg of apomorphine subcutaneously is administered.
*J. Pharmacol. Exp. Ther., 154(4), pp. 449–516 (1966).

6.3 Test Results with Fenfluramine

6.3.1 DL-Fenfluramine Prior to Cisplatin

Utilizing Test Procedure A, supra, and administering 5.0 mg/kg of 1-(3'-trifluoromethylphenyl)-2-ethylaminopropane hydrochloride intravenously 30 minutes prior to the administration of 3.0 mg/kg cisplatin intravenously, 72% inhibition was seen in the number of emetic episodes experienced by dogs receiving 1-(3'-trifluoromethylphenyl)-2-ethylamino propane hydrochloride when compared to dogs receiving control (distilled water).

6.3.2 DL-Fenfluramine After Cisplatin

Utilizing Test Procedure A, supra, and administering 5.0 mg/kg of 1-(3'-trifluoromethylphenyl)-2-ethylamino propane intravenously 60 minutes after administration of 3.0 mg/kg cisplatin intravenously, 78% inhibition was seen in the number of emetic episodes experienced by dogs receiving 1-(3'-trifluoromethylphenyl)-2-ethylamino propane hydrochloride when compared to dogs receiving control (distilled water).

6.3.3 DL-Fenfluramine After Dacarbazine

Utilizing Test Procedure A, supra, and administering 5.0 mg/kg of 1-(3'-trifluoromethylphenyl)-2-ethylamino propane intravenously 60 minutes after administering 30.0 mg/kg of dacarbazine intravenously, 84% inhibition was seen in the number of emetic episodes experienced by dogs receiving 1-(3'-trifluoromethylphenyl)-2-ethylamino propane hydrochloride when compared to dogs receiving control (distilled water).

6.3.4 DL-Fenfluramine After Protoveratrine A

Utilizing Test Procedure A, supra, and administering 5.0 mg/kg of 1-(3'-trifluoromethylphenyl)-2-ethylamino propane intravenously 60 minutes after administration of 100 mg/kg Protoveratrine A orally, 78% inhibition was seen in the number of emetic episodes experienced by dogs received 1-(3'-trifluoromethylphenyl)-2-ethylamino propane hydrochloride when compared to dogs receiving control (distilled water).

6.3.5 DL-Fenfluramine After Copper Sulfate

Utilizing Test Procedure A, supra, and administering 5.0 mg/kg of 1-(3'-trifluoromethylphenyl)-2-ethylamino propane intravenously 60 minutes after administering 20 mg/kg of copper sulfate orally, 68% inhibition was seen in the number of emetic episodes experienced by dogs receiving 1-(3'-trifluoromethylphenyl)-2-ethylamino propane hydrochloride when compared to dogs receiving control (distilled water).

6.3.6 DL-Fenfluramine Prior to Apomorphine

Utilizing Test Procedure B, supra, and administering 5.0 mg/kg of 1-(3'-trifluoromethylphenyl)-2-ethylamino propane hydrochloride intravenously 30 minutes prior to the administration of 100 µg/kg of apomorphine subcutaneously, 91% inhibition was seen in the number of emetic episodes experienced by dogs receiving 1-(3'-trifluoromethylphenyl)-2-ethylaminopropane when compared to the number of emetic episodes experienced by controls.

6.3.7 D-Fenfluramine Prior to Cisplatin

Utilizing Test Procedure A, supra, and administering (d)-1-(3'-trifluoromethylphenyl)-2-ethylaminopropane hydrochloride (3.16 mg/kg, IV) 30 min prior to cisplatin (3.0 mg/kg, IV) greater than 90% inhibition of emetic episodes occurred when compared with the control group.

6.3.8 L-Fenfluramine Prior to Cisplatin

Utilizing Test Procedure A, supra, and administering (1)-1-(3'-trifluoromethylphenyl)-2-ethylaminopropane (3.16 mg/kg, IV) 30 min prior to cisplatin (3.0 mg/kg, IV) greater than 70% inhibition of emetic episodes occurred when compared with the control group.

6.4 Test Results with Norfenfluramine

6.4.1 DL-Norfenfluramine Prior to Cisplatin

Utilizing Test Procedure A, supra, and administering 1-(3'-trifluoromethylphenyl)-2-aminopropane hydrochloride (5.0 mg/kg, IV) 30 min prior to cisplatin (3.0 mg/kg, IV) greater than 70% inhibition of emetic episodes occurred when compared with the control group.

6.4.2 DL-Norfenfluramine Prior to Apomorphine

Utilizing Test Procedure B, supra, and administering 1-(3'-trifluoromethylphenyl)-2-aminopropane hydrochloride 30 min prior to administration of apomorphine inhibited greater than 90% of emetic episodes when compared with the control group.

6.5 Test Results with P-Chlorophenylalanine

6.5.1 DL-p-chlorophenylalanine Prior to Cisplatin

Utilizing Test Procedure A, supra and administering DL-p-chlorophenylalanine orally (100 mg/kg) once a day for 9 consecutive days prior to the administration of cisplatin (3.0 mg/kg, IV) greater than 70% inhibition of emetic episodes occurred when compared with the control group.

6.5 CONTROL OF EMESIS BY FORMULA I COMPOUNDS

6.5.1 Cisplatin Induced Emesis

When an effective antiemetic amount of one of the following Formula I compounds (sources provided above):

DL-4-bromophenylalanine,
L-4-chlorophenylalanine,
DL-4-chlorophenylalanine ethyl ester hydrochloride,
DL-4-chlorophenylalanine methyl ester hydrochloride,
DL-2-fluorophenylalanine,
DL-3-fluorophenylalanine,
DL-4-fluorophenylalanine,
D-4-fluorophenylalanine,
L-4-fluorophenylalanine,
D-4-iodophenylalanine,
DL-4- chloroamphetamine hydrochloride,
4-bromophenethylamine,
2-(2-chlorophenyl)ethylamine,
2-(4-chlorophenyl)ethylamine,
4-fluorophenethylamine hydrochloride,
2-(3-chlorophenyl)ethylamine,
1-(4'-trifluoromethylphenyl)-2-aminopropane,
1-(4'-trifluoromethylphenyl)-2-aminopropane hydrochloride,
1-(4'-fluorophenyl)-3,3,3-trifluoro-2-aminopropane,
1-(4'-fluorophenyl)-3,3,3-trifluoro-2-aminopropane hydrochloride,
1-(4'fluorophenyl)-2-dimethylaminopropane,
1-(4'-fluorophenyl)-2-dimethylaminopropane hydrochloride,
1-(3'-trifluoromethylphenyl)-2-dimethylaminopropane,
1-(3'-trifluoromethylphenyl)-2-dimethylaminopropane hydrochloride,
1-(4'-fluorophenyl)-2-ethylaminopropane,
1-(4'-fluorophenyl)-2-ethylaminopropane hydrochloride,
1-(2'-fluorophenyl)-2-ethylaminopropane,
1-(2'-fluorophenyl)-2-ethylaminopropane hydrochloride,
1-(4'-fluorophenyl)-2-butylaminopropane,
1-(4'-fluorophenyl)-2-butylaminopropane hydrochloride,
1-(4'-trifluoromethylphenyl)-2-ethylaminopropane,
1-(4'-trifluoromethylphenyl)-2-ethylaminopropane hydrochloride,
1-(3'-trifluoromethylphenyl)-2-ethylaminopropane,
1-(p-trifluoromethylphenyl)-2-aminopropane hydrochloride,
p-trifluoromethylphenylethylamine,
p-trifluoromethylphenylethylamine tartarate,
o-trifluoromethylphenylethylamine, o-trifluoromethylphenylethylamine acetate,
DL-2-bromoamphetamine,
DL-3-bromoamphetamine,
DL-4-bromoamphetamine,
DL-2-chloroamphetamine,
DL-3-chloroamphetamine,
DL-4-chloroamphetamine,
DL-4-bromophenylalanine ethyl ester,
L-4-chlorophenylalanine ethyl ester,
DL-2-fluorophenylalanine ethyl ester,
DL-3-fluorophenylalanine ethyl ester,
DL-4-fluorophenylalanine ethyl ester,
DL-4-fluorophenylalanine ethyl ester,
D-4-fluorophenylalanine ethyl ester,
L4-fluorophenylalanine ethyl ester,
D-4-iodophenylalanine ethyl ester,
DL-4-chlorophenylalanine t-butyl ester,
DL-2-trifluoromethylphenylalanine t-butyl ester,
DL-3-trifluoromethylphenylalanine t-butyl ester,
DL-4-trifluoromethylphenylalanine t-butyl ester,
DL-2-bromophenylalanine t-butyl ester,
DL-3-bromophenylalanine t-butyl ester,
DL-4-bromophenylalanine t-butyl ester,
DL-2-chlorophenylalanine t-butyl ester,
DL-3-chlorophenylalanine t-butyl ester,
DL-2-fluorophenylalanine t-butyl ester,
DL-3-fluorophenylalanine t-butyl ester,
DL-4-fluorophenylalanine t-butyl ester,
DL-2-iodophenylalanine t-butyl ester,
(d)norfenfluramine hydrochloride,
(l)norfenfluramine hydrochloride,
(l)-1-(m-trifluoromethylphenyl)-2-ethylaminopropane hydrochloride, or
(d)-1-(m-trifluoromethylphenyl)-2-ethylaminopropane hydrochloride,
is administered intravenously in Test Procedure A, supra, either 30 minutes prior to or 60 minutes after intravenously administering 5.0 mg/kg cisplatin, control of emesis is expectable.

6.5.2 Dacarbazine or Other Antineoplastic Induced Emesis

When an effective antiemetic amount of one of the following Formula I compounds (sources provided above):
DL-4-bromophenylalanine,
DL-4-chlorophenylalanine,
DL-4-chlorophenylalanine ethyl ester hydrochloride,
DL-4-chlorophenylalanine methyl ester hydrochloride,
DL-2-fluorophenylalanine,
DL-3-fluorophenylalanine,
DL-4-fluorophenylalanine,
D-4-fluorophenylalanine,
L-4-fluorophenylalanine,
D-4-iodophenylalanine,
DL-4-chloroamphetamine hydrochloride,
4-bromophenethylamine,
2-(2-chlorophenyl)ethylamine, 2-(4-chlorophenyl)ethylamine,
4-fluorophenethylamine hydrochloride,
2-(3-chlorophenyl)ethylamine,
1-(4'-trifluoromethylphenyl)-2-aminopropane,
1-(4'-trifluoromethylphenyl)-2-aminopropane hydrochloride,
1-(4'-trifluorophenyl)-3,3,3-trifluoro-2-aminopropane,
1-(4'-fluorophenyl)-3,3,3-trifluoro-2-aminopropane hydrochloride,
1-(4'-fluorophenyl)-2-dimethylaminopropane,
1-(4'-fluorophenyl)-2-dimethylaminopropane hydrochloride,
1-(3'-trifluoromethylphenyl)-2-dimethylaminopropane,
1-(3'-trifluoromethylphenyl)-2-dimethylaminopropane hydrochloride,
1-(4'-fluorophenyl)-2-ethylaminopropane,
1-(4'-fluorophenyl)-2-ethylaminopropane hydrochloride,
1-(2'-fluorophenyl)-2-ethylaminopropane,
1-(2'-fluorophenyl)-2-ethylaminopropane hydrochloride,
1-(4'-fluorophenyl)-2-butylaminopropane,
1(4'-fluorophenyl)-2-butylaminopropane hydrochloride,
1-(4'-trifluoromethylphenyl)-2-ethylaminopropane,
1-(4'-trifluoromethylphenyl)-2-ethylaminopropane hydrochloride,
1-(3'-trifluoromethylphenyl)-2-ethylaminopropane,
1-(p-trifluoromethylphenyl)-2-aminopropane hydrochloride,
p-trifluoromethylphenylethylamine,
p-trifluoromethylphenylethylamine tartarate,
o-trifluoromethylphenylethylamine,
o-trifluoromethylphenylethylamine acetate,
DL-2-bromoamphetamine,
DL-3-bromoamphetamine,
DL-4-bromoamphetamine,
DL-2-chloroamphetamine,
DL-3-chloroamphetamine,
DL-4-chloroamphetamine,
DL-4-bromophenylalanine ethyl ester,
L-4-chlorophenylalanine ethyl ester,
DL-2-fluorophenylalanine ethyl ester,
DL-3-fluorophenylalanine ethyl ester,
DL-4-fluorophenylalanine ethyl ester,
DL-4-fluorophenylalanine ethyl ester,
D-4-fluorophenylalanine ethyl ester,
L-4-fluorophenylalanine ethyl ester,
D-4-iodophenylalanine ethyl ester,
DL-4-chlorophenylalanine t-butyl ester,
DL-2-trifluoromethylphenylalanine t-butyl ester,
DL-3-trifluoromethylphenylalanine t-butyl ester,
DL-4-trifluoromethylphenylalanine t-butyl ester,
DL-2-bromophenylalanine t-butyl ester,
DL-3-bromophenylalanine t-butyl ester,
DL-4-bromophenylalanine t-butyl ester,
DL-2-chlorophenylalanine t-butyl ester,
DL-3-chlorophenylalanine t-butyl ester,
DL-2-fluorophenylalanine t-butyl ester,
DL-3-fluorophenylalanine t-butyl ester,
DL-4-fluorophenylalanine t-butyl ester,
DL-2-iodophenylalanine t-butyl ester,
(d)norfenfluramine hydrochloride,
(−)norfenfluramine hydrochloride,
l-1-(m-trifluoromethylphenyl)-2-ethylaminopropane hydrochloride, and
dl-(m-trifluoromethylphenyl)-2-ethylaminopropane hydrochloride,
is administered intravenously as in Test Procedure A, supra, in conjunction with a chemotherapeutic amount of one of the following antineoplastic agents capable of causing emesis:
dacarbazine,
nitrogen mustard,
cyclophosphamide,
dactinomycin,
6-thioguanidine,
carmustine, lomustine,
methotrexate,
5-fluorouracil,
vinblastine,
aminoglutethimide,
asparaginase,
bleomycin,
busulfan,
cytarabine hydrochloride,
daunorubicin,
doxorubicin,
estramustine phosphate sodium,
etoposide,
floxuridine,
fluorouracil,
hydroxyurea,
mercaptopurine,
mitomycin,
mitotane,
plicamycin,
procarbazine hydrochloride,
streptozocin,
tamoxifen citrate, or
triethylenethiophosphoramide
control emesis is expectable.

6.5.3 Apomorphine Induced Emesis

When an effective antiemetic amount of one of the following Formula I compounds (sources provided above):
DL-4-bromophenylalanine,
DL-4-chlorophenylalanine,
DL-4-chlorophenylalanine ethyl ester hydrochloride,
DL-4-chlorophenylalanine methyl ester hydrochloride,
DL-2-fluorophenylalanine,
DL-3-fluorophenylalanine,
DL-4-fluorophenylalanine,
D-4-fluorophenylalanine,
L-4-fluorophenylalanine,
jD-4-iodophenylalanine,
DL-4-chloroamphetamine hydrochloride,
4-bromophenethylamine,
2-(2-chlorophenyl)ethylamine,
2-(4-chlorophenyl)ethylamine,
4-fluorophenethylamine hydrochloride,
2-(3-chlorophenyl)ethylamine,
1-(4'-trifluoromethylphenyl)-2-aminopropane,
1-(4'-trifluoromethylphenyl)-2-aminopropane hydrochloride,
1-(4'-trifluorophenyl)-3,3,3,-trifluoro-2-aminopropane,
1-(4'-fluorophenyl)-3,3,3-trifluoro-2-aminopropane hydrochloride,
1-(4'-fluorophenyl)-2-dimethylaminopropane,
1-(4'-fluorophenyl)-2-dimethylaminopropane hydrochloride,
1-(3'-trifluoromethylphenyl)-2-dimethylaminopropane,
1-(3'-trifluoromethylphenyl)-2-dimethylaminopropane hydrochloride,
1-(4'-fluorophenyl)-2-ethylaminopropane,
1-(4'-fluorophenyl)-2-ethylaminopropane hydrochloride,
1-(2'-fluorophenyl)-2-ethylaminopropane,
1-(2'-fluorophenyl)-2-ethylaminopropane hydrochloride,
1-(4'-fluorophenyl)-2-butylaminopropane,
1-(4'-fluorophenyl)-2-butylaminopropane hydrochloride,
1-(4'-trifluoromethylphenyl)-2-ethylaminopropane,
1-(4'-trifluoromethylphenyl)-2-ethylaminopropane hydrochloride,
1-(3'-trifluoromethylphenyl)-2-ethylaminopropane,
1-(p-trifluoromethylphenyl)-2-aminopropane hydrochloride,
p-trifluoromethylphenylethylamine,
p-trifluoromethylphenylethylamine tartarate,
o-trifluoromethylphenylethylamine,
o-trifluoromethylphenylethylamine acetate,
DL-2-bromoamphetamine,
DL-3-bromoamphetamine,
DL-4-bromoamphetamine,
DL-2-chloroamphetamine,
DL-3-chloroamphetamine,
DL-4-chloroamphetamine,
DL-4-bromophenylalanine ethyl ester,
L-4-chlorophenylalanine ethyl ester,
DL-2-fluorophenylalanine ethyl ester,
DL-3-fluorophenylalanine ethyl ester,
DL-4-fluorophenylalanine ethyl ester,
DL-4-fluorophenylalanine ethyl ester,
D-4-fluorophenylalanine ethyl ester,
L-4-fluorophenylalaine ethyl ester,
D-4-iodophenylalanine ethyl ester,
DL-4-chlorophenylalanine t-butyl ester,
DL-2-trifluoromethylphenylalanine t-butyl ester,
DL-3-trifluoromethylphenylalanine t-butyl ester,
DL-4-trifluoromethylphenylalanine t-butyl ester,
DL-2-bromophenylalanine t-butyl ester,
DL-3-bromophenylalanine t-butyl ester,
DL-4-bromophenylalanine t-butyl ester,
DL-2-chlorophenylalanine t-butyl ester,
DL-3-chlorophenylalanine t-butyl ester,
DL-2-fluorophenylalanine t-butyl ester,
DL-3-fluorophenylalanine t-butyl ester,
DL-4-fluorophenylalanine t-butyl ester,
DL-2-iodophenylalanine t-butyl ester,
(d)norfenfluramine hydrochloride,
(l)norfenfluramine hydrochloride,
(l)-1-(m-trifluoromethylphenyl)-2-ethylaminopropane hydrochloride, or
(d)-1-(m-trifluoromethylphenyl)-2-ethylaminopropane hydrochloride,
is administered as in Test Procedure B, supra, control of emesis is expectable.

6.5.3 Copper Sulfate Induced Emesis

When an effective antiemetic amount of one of the following Formula I compounds (sources provided above):
DL-4-bromophenylalanine,
L-4-chlorophenylalanine,
DL-4-chlorophenylalanine ethyl ester hydrochloride,
DL-4-chlorophenylalanine methyl ester hydrochloride,
DL-2-fluorophenylalanine,
DL-3-fluorophenylalanine,
DL-4-fluorophenylalanine,
D-4-fluorophenylalanine,
L-4-fluorophenylalanine,
D-4-iodophenylalanine,
DL-4-chloroamphetamine hydrochloride,
4-bromophenethylamine,
2-(2-chlorophenyl)ethylamine,
2-(4-chlorophenyl)ethylamine,
4-fluorophenethylamine hydrochloride,
2-(3-chlorophenyl)ethylamine,
1-(4'-trifluoromethylphenyl)-2-aminopropane, 1-(4'-trifluoromethylphenyl)-2-aminopropane hydrochloride,
1-(4'-fluorophenyl)-3,3,3-trifluoro-2-aminopropane,
1-(4'-fluorophenyl)-3,3,3-trifluoro-2-aminopropane hydrochloride,
1-(4'-fluorophenyl)-2-dimethylaminopropane,
1-(4'-fluorophenyl)-2-dimethylaminopropane hydrochloride,
1-(3'-trifluoromethylphenyl)-2-dimethylaminopropane,
1-(3'-trifluoromethylphenyl)-2-dimethylaminopropane hydrochloride,
1-(4'-fluorophenyl)-2-ethylaminopropane,
1-(4'-fluorophenyl)-2-ethylaminopropane hydrochloride,
1-(2'-fluorophenyl)-2-ethylaminopropane,
1-(2'-fluorophenyl)-2-ethylaminopropane hydrochloride,
1-(4'-fluorophenyl)-2-butylaminopropane,
1-(4'-fluorophenyl)-2-butylaminopropane hydrochloride,
1-(4'-trifluoromethylphenyl)-2-ethylaminopropane,
1-(4'-trifluoromethylphenyl)-2-ethylaminopropane hydrochloride,
1-(3'-trifluoromethylphenyl)-2-ethylaminopropane,
1-(p-trifluoromethylphenyl)-2-aminopropane hydrochloride,
p-trifluoromethylphenylethylamine,
p-trifluoromethylphenylethylamine tartarate,
o-trifluoromethylphenylethylamine,
o-trifluoromethylphenylethylamine acetate,
DL-2-bromoamphetamine,
DL-3-bromoamphetamine,
DL-4-bromoamphetamine,
DL-2-chloroamphetamine,
DL-3-chloroamphetamine,
DL-4-chloroamphetamine,
DL-4-bromophenylalanine ethyl ester,
L-4-chlorophenylalanine ethyl ester,
DL-2-fluorophenylalanine ethyl ester,
DL-3-fluorophenylalanine ethyl ester,
DL-4-fluorophenylalanine ethyl ester,
DL-4-fluorophenylalanine ethyl ester,
D-4-fluorophenylalanine ethyl ester,
L-4-fluorophenylalanine ethyl ester,
D-4-iodophenylalanine ethyl ester,
DL-4-chlorophenylalanine t-butyl ester,
DL-2-trifluoromethylphenylalanine t-butyl ester,
DL-3-trifluoromethylphenylalanine t-butyl ester,
DL-4-trifluoromethylphenylalanine t-butyl ester,
DL-2-bromophenylalanine t-butyl ester,
DL-3-bromophenylalanine t-butyl ester,
DL-4-bromophenylalanine t-butyl ester,
DL-2-chlorophenylalanine t-butyl ester,
DL-3-chlorophenylalanine t-butyl ester,
DL-2-fluorophenylalanine t-butyl ester,
DL-3-fluorophenylalanine t-butyl ester,
DL-4-fluorophenylalanine t-butyl ester,
DL-2-iodophenylalanine t-butyl ester,
(d)norfenfluramine hydrochloride,
(l)norfenfluramine hydrochloride,
(l)-1-(m-trifluoromethylphenyl)-2-ethylaminopropane hydrochloride, or
(d)-1-(m-trifluoromethylphenyl)-2-ethylaminopropane hydrochloride,
is administered intravenously in Test Procedure A, supra, either 30 minutes prior to or 60 minutes after administering 20.0 mg/kg copper sulfate orally, control of emesis is expectable.

6.5.4 Protoveratrine A Induced Emesis

When an effective antiemetic amount of one of the following Formula I compounds (sources provided above):
DL-4-bromophenylalanine,
L-4-chlorophenylalanine,
DL-4-chlorophenylalanine ethyl ester hydrochloride,
DL-4-chlorophenylalanine methyl ester hydrochloride,
DL-2-fluorophenyolalanine,
DL-3-fluorophenylalanine,
DL-4-fluorophenylalanine,
D-4-fluorophenylalanine,
L-4-fluorophenylalanine,
D-4-iodophenylalanine,
DL-4-chloroamphetamine hydrochloride,
4-bromophenethylamine,
2-(2-chlorophenyl)ethylamine,
2-(4-chlorophenyl)ethylamine,
4-fluorophenethylamine hydrochloride,
2-(3-chlorophenyl)ethylamine,
1-(4'-trifluoromethylphenyl)-2-aminopropane,
1-(4'-trifluoromethylphenyl)-2-aminopropane hydrochloride,
1-(4'-fluorophenyl)-3,3,3-trifluoro-2-aminopropane,
1-(4'-fluorophenyl)-3,3,3-trifluoro-2-aminopropane hydrochloride,
1-(4'-fluorophenyl)-2-dimethylaminopropane,
1-(4'-fluorophenyl)-2-dimethylaminopropane hydrochloride,
1-(3'-trifluoromethylphenyl)-2-dimethylaminopropane,
1-(3'-trifluoromethylphenyl)-2-dimethylaminopropane hydrochloride,
1-(4'-fluorophenyl)-2-ethylaminopropane,
1-(4'-fluorophenyl)-2-ethylaminopropane hydrochloride,
1-(2'-fluorophenyl)-2-ethylaminopropane,
1-(2'-fluorophenyl)-2-ethylaminopropane hydrochloride,
1-(4'-fluorophenyl)-2-butylaminopropane,
1-(4'-fluorophenyl)-2-butylaminopropane hydrochloride,
1-(4'-trifluoromethylphenyl)-2-ethylaminopropane,
1-(4'-trifluoromethylphenyl)-2-ethylaminopropane hydrochloride,
1-(3'-trifluoromethylphenyl)-2-ethylaminopropane,
1-(p-trifluoromethylphenyl)-2-aminopropane hydrochloride,
p-trifluoromethylphenylethylamine,
p-trifluoromethylphenylethylamine tartarate,
o-trifluoromethylphenylethylamine,
o-trifluoromethylphenylethylamine acetate,
DL-2-bromoamphetamine,
DL-3-bromoamphetamine,
DL-4-bromoamphetamine,
DL-2-chloroamphetamine,
DL-3-chloroamphetamine,
DL-4-chloroamphetamine,
DL-4-bromophenylalanine ethyl ester,
L-4-chlorophenylalanine ethyl ester,
DL-2-fluorophenylalanine ethyl ester,
DL-3-fluorophenylalanine ethyl ester,
DL-4-fluorophenylalanine ethyl ester,
DL-4-fluorophenylalanine ethyl ester,
D-4-fluorophenylalanine ethyl ester,
L-4-fluorophenylalanine ethyl ester,
D-4-iodophenylalanine ethyl ester,
DL-4-chlorophenylalanine t-butyl ester, DL-2-trifluoromethylphenylalanine t-butyl ester,
DL-3-trifluoromethylphenylalanine t-butyl ester,
DL-4-trifluoromethylphenylalanine t-butyl ester,
DL-2-bromophenylalanine t-butyl ester,
DL-3-bromophenylalanine t-butyl ester,
DL-4-bromophenylalanine t-butyl ester,
DL-2-chlorophenylalanine t-butyl ester,
DL-3-chlorophenylalanine t-butyl ester,
DL-2-fluorophenylalanine t-butyl ester,
DL-3-fluorophenylalanine t-butyl ester,
DL-4-fluoropheylalanine t-butyl ester,
DL-2-iodophenylalanine t-butyl ester,
(d)norfenfluramine hydrochloride,
(l)norfenfluramine hydrochloride,
(l)-1-(m-trifluoromethylphenyl)-2-ethylaminopropane hydrochloride, or
(d)-1-(m-trifluoromethylphenyl)-2-ethylaminopropane hydrochloride,
is administered intravenously in Test Procedure A, supra, either 30 minutes prior to or 60 minutes after administering 100.0 mg/kg of Protoveratrine A orally, control of emesis is expectable.

7. Pharmaceutical Method and Compositions

Generally the method of controlling emesis in accordance with this invention comprises administering at least one of the compounds of Formula I in association with a pharmaceutical carrier or excipient. The compounds may be presented in a therapeutic composition suitable for oral, rectal, intravenous, subcutaneous, intramuscular, or parenteral administration.

Thus, for example, compositions for oral administration are preferably solids and can take the form of capsules, tablets or coated tablets containing carriers conveniently used in the pharmaceutical art. Suitable tableting carriers or excipients include lactose, potato and maize starches, talc, gelatin and stearic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be obtained consistent with the dosage form employed. The exact individual dosages, as well as daily dosages, will, of course, be determined according to standard medical principles under the direction of a physician or veterinarian. Advantageously, the compounds of Formula I may be administered once a day in a single unit dosage, or if necessary, in repeated dosages until satisfactory response is obtained. The average daily dosage being from about 20 to about 120 mg of active medication, advantageously from about 20 to about 60 mg. The pharmaceutical compositions contain about 20 to about 60 mg of active medicament per unit.

Examples of unit dosage compositions are as follows:

| Capsules | |
|---|---|
| Ingredients | Per Cap. |
| 1. Active ingredient | 20.0 mg |
| 2. Lactose | 146.0 mg |
| 3. Magnesium Stearate | 4.0 mg |
| | 170.0 mg |

Procedure

Step 1. Blend ingredients 1, 2 and 3.
Step 2. Pass blend from Step 1 through a No. 30 mesh screen (0.59 mm) and blend again.
Step 3. Fill powder blend from Step 2 into No. 1 hard gelatin capsules.

| Ingredients | Mg/Tab. |
|---|---|
| Tablets (20 mg) | |
| 1. Active ingredient | 20.0 mg |
| 2. Corn starch | 20.0 mg |
| 3. Alginic acid | 20.0 mg |
| 4. Socium alginate | 20.0 mg |
| 5. Magnesium stearate | 1.3 mg |
| | 81.3 mg |
| Tablets (40 mg) | |
| 1. Active ingredient | 40.0 mg |
| 2. Milo starch | 20.0 mg |
| 3. Corn starch | 38.0 mg |
| 4. Lactose | 90.0 mg |
| 5. Magnesium stearate | 2.0 mg |
| | 190.0 mg |

Procedure

Step 1. Blend ingredients 1, 2 and 3 and 4.
Step 2. Add sufficient water portionwise to the blend from Step 1 with careful stirring after each addition. Such additions of water and stirring continue until the mass is of a consistency to permit its conversion to wet granules.
Step 3. The wet mass prepared in Step 2 is converted to granules by passing it through an oscillating granulator, using a #8-mesh (2.36 mm) screen.
Step 4. The wet granules prepared in Step 3 are dried in an oven at 140° F.
Step 5. Dried granules from Step 4 are passed through an oscillating granulator, using a No. 10-mesh (2.00 mm) screen.
Step 6. Lubricate the dry granules from Step 5 by blending with ingredient No. 5.
Step 7. The lubricated granules from Step 6 are compressed on a suitable tablet press.

| Intravenous Injection | |
|---|---|
| Ingredients | Per ml. |
| 1. Active ingredient | 20 mg |
| 2. Isotonic pH 4.0 buffer solution q.s. to | 5.0 ml |

Procedure

Step 1. Dissolve the active ingredient in the buffer solution.
Step 2. Aseptically filter the solution from Step 1.
Step 3. The sterile solution is now aseptically filled into sterile ampuls.

Step 4. The ampuls are sealed under aseptic conditions.

| Intramuscular Injection | |
|---|---|
| Ingredients | Per ml. |
| 1. Active ingredient | 40 mg |
| 2. Isotonic pH 4.0 buffer solution q.s. to | 5.0 ml |

Procedure

Step 1. Dissolve the active ingredient in the buffer solution.
Step 2. Aseptically filter the solution from Step 1.
Step 3. The sterile solution is now aseptically filled into sterile ampuls.
Step 4. The ampuls are sealed under aseptic conditions.

| Suppositories | |
|---|---|
| Ingredients | Per Supp. |
| 1. Active ingredient | 60.0 mg |
| 2. Polyethylene Glycol 1000 | 1350.0 mg |
| 3. Polyethylene Glycol 4000 | 450.0 mg |
| | 1860.0 mg |

Procedure

Step 1. Melt ingredients No. 2 and No. 3 together and stir until uniform.
Step 2. Dissolve ingredient No. 1 in the molten mass from Step 1 and stir until uniform.
Step 3. Pour the molten mass from Step 2 into suppository molds and allow to cool.
Step 4. Remove the suppositories from molds and wrap.

Various modifications and equivalents will be apparent to one skilled in the art, and may be made in the compounds, compositions, and methods of the present invention without departing from the spirit or scope thereof and it is therefore to be understood that the invention is to be limited only by the scope of the appended claims.

What is claimed is:

1. A method for treating mammals for emesis which method comprises internally administering to a mammal in need thereof an emesis inhibiting amount of a compound having the formula:

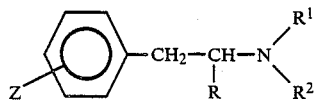

wherein,
R is hydrogen, loweralkyl, trifluoromethyl, carboxyl or loweralkoxycarbonyl,
$R^1$ and $R^2$ are hydrogen or loweralkyl;
Z is, same or different, trifluoromethyl or halogen; optical isomers thereof;
and pharmaceutically acceptable salts thereof.

2. The method of claim 1 wherein the compound administered is DL-fenfluramine or a pharmaceutically acceptable salt thereof.

3. The method of claim 1 wherein the compound administered is D-fenfluramine or a pharmaceutically acceptable salt thereof.

4. The method of claim 1 wherein the compound administered is L-fenfluramine or a pharmaceutically acceptable salt thereof.

5. The method of claim 1 wherein the compound administered is DL-norfenfluramine or a pharmaceutically acceptable salt thereof.

6. The method of claim 1 wherein the compound administered is D-norfenfluramine or a pharmaceutically acceptable salt thereof.

7. The method of claim 1 wherein the compound administered is L-norfenfluramine or a pharmaceutically acceptable salt thereof.

8. The method of claim 1 wherein the compound administered is DL-p-chlorophenylalanine or a pharmaceutically acceptable salt thereof.

9. A method for treating mammals for emesis which method comprises internally administering to a mammal in need thereof an emesis inhibiting amount of a compound having the formula:

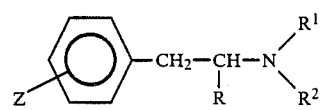

wherein,
R is hydrogen, loweralkyl, or trifluoromethyl,
$R^1$ and $R^2$, the same or different, hydrogen or loweralkyl;
Z is trifluoromethyl or halogen; optical isomers thereof; and
pharmaceutically acceptable salts thereof.

10. The method of claim 9 wherein the compound administered is DL-fenfluramine or a pharmaceutically acceptable salt thereof.

11. The method of claim 9 wherein the compound administered is D-fenfluramine or a pharmaceutically acceptable salt thereof.

12. The method of claim 9 wherein the compound administered is L-fenfluramine or a pharmaceutically acceptable salt thereof.

13. The method of claim 9 wherein the compound administered is DL-norfenfluramine or a pharmaceutically acceptable salt thereof.

14. The method of claim 9 wherein the compound administered is D-norfenfluramine or a pharmaceutically acceptable salt thereof.

15. The method of claim 9 wherein the compound administered is L-norfenfluramine or a pharmaceutically acceptable salt thereof.

16. A method for treating mammals for emesis which method comprises internally administering to a mammal in need thereof an emesis inhibiting amount of a compound having the formula:

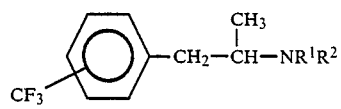

wherein
$R^1$ and $R^2$, same or different, are hydrogen or loweralkyl;
optical isomers thereof; and pharmaceutically acceptable salts thereof.

17. The method of claim 16 wherein the compound administered is DL-fenfluramine or a pharmaceutically acceptable salt thereof.

18. The method of claim 16 wherein the compound administered is D-fenfluramine or a pharmaceutically acceptable salt thereof.

19. The method of claim 16 wherein the compound administered is L-fenfluramine or a pharmaceutically acceptable salt thereof.

20. The method of claim 16 wherein the compound administered is DL-norfenfluramine or a pharmaceutically acceptable salt thereof.

21. The method of claim 16 wherein the compound administered is D-norfenfluramine or a pharmaceutically acceptable salt thereof.

22. The method of claim 16 wherein the compound administered is L-norfenfluramine or a pharmaceutically acceptable salt thereof.

* * * * *